United States Patent
Sarac

(10) Patent No.: US 9,956,070 B2
(45) Date of Patent: May 1, 2018

(54) PERCUTANEOUS ENDOVASCULAR APPARATUS FOR REPAIR OF ANEURYSMS AND ARTERIAL BLOCKAGES

(71) Applicant: TMT SYSTEMS, Milford, CT (US)

(72) Inventor: Timur P. Sarac, Cuyahoga, OH (US)

(73) Assignee: TMT SYSTEMS, Milford, CT (US)

(*) Notice: Subject to any disclaimer, the term of this patent is extended or adjusted under 35 U.S.C. 154(b) by 0 days. days.

(21) Appl. No.: 14/937,909

(22) Filed: Nov. 11, 2015

(65) Prior Publication Data

US 2016/0058546 A1    Mar. 3, 2016

Related U.S. Application Data

(63) Continuation of application No. 11/484,331, filed on Jul. 10, 2006, which is a continuation-in-part of (Continued)

(51) Int. Cl.
*A61F 2/07*    (2013.01)
*A61F 2/89*    (2013.01)
(Continued)

(52) U.S. Cl.
CPC ............ *A61F 2/07* (2013.01); *A61F 2/848* (2013.01); *A61F 2/89* (2013.01);
(Continued)

(58) Field of Classification Search
CPC ........ A61F 2/07–2002/077; A61F 2/04; A61F 2002/825; A61F 2002/828; A61F 2/89;
(Continued)

(56) References Cited

U.S. PATENT DOCUMENTS

| 5,226,913 A | 7/1993 | Pinchuk |
| 5,456,713 A | 10/1995 | Chuter |

(Continued)

FOREIGN PATENT DOCUMENTS

| EP | 0947179 A2 | 6/1999 |
| EP | 1138279 A2 | 4/2001 |
| WO | 2004008996 A1 | 1/2004 |

OTHER PUBLICATIONS

DACRON status printout from the USPTO Trademark Electronic Seach System, printed from wed on Jan. 5, 2009.
(Continued)

*Primary Examiner* — Paul Prebilic
(74) *Attorney, Agent, or Firm* — Farber LLC

(57) ABSTRACT

An endovascular apparatus is provided for treating the effects of vascular disease including aneurysms and arterial blockages using a percutaneous, minimally invasive technique. In one embodiment the endovascular apparatus includes a tubular sleeve having a cranial end, a first caudal branch, and a second caudal branch such that the tubular sleeve is shaped like an upside down "Y." The apparatus further includes at least one expandable attachment device attached to the tubular sleeve for securing the endovascular apparatus to an interior wall of a vessel. The at least one expandable attachment device includes a plurality of telescoping segments similar to the telescoping segments of a presentation pointer. Accordingly, during percutaneous insertion of the endovascular apparatus into a patient the attachment device can be collapsed into a small profile. Once positioned at the site of the aneurysm the telescoping attachment device can be expanded to hold the endovascular apparatus in place adjacent the inner lumen wall.

12 Claims, 10 Drawing Sheets

Related U.S. Application Data application No. 10/624,864, filed on Jul. 22, 2003, now Pat. No. 7,101,393.

(60) Provisional application No. 60/397,745, filed on Jul. 22, 2002.

(51) Int. Cl.
*A61F 2/848* (2013.01)
*A61F 2/06* (2013.01)
*A61F 2/82* (2013.01)

(52) U.S. Cl.
CPC ... *A61F 2002/065* (2013.01); *A61F 2002/075* (2013.01); *A61F 2002/826* (2013.01); *A61F 2220/005* (2013.01); *A61F 2220/0016* (2013.01); *A61F 2220/0075* (2013.01); *A61F 2230/005* (2013.01); *A61F 2230/0017* (2013.01); *A61F 2230/0054* (2013.01); *A61F 2250/001* (2013.01); *A61F 2250/0007* (2013.01)

(58) Field of Classification Search
CPC .......... A61F 2210/00; A61F 2220/0008; A61F 2250/0058; A61F 2250/0065; A61F 2250/0067–2250/0069; A61F 2220/0016; A61F 2230/0023; A61F 2230/0056
USPC ...................................................... 623/1.35
See application file for complete search history.

(56) References Cited

U.S. PATENT DOCUMENTS

| | | | |
|---|---|---|---|
| 5,681,346 A | 10/1997 | Orth et al. | |
| 5,693,088 A * | 12/1997 | Lazarus | A61F 2/07 606/195 |
| 5,755,777 A | 5/1998 | Chuter | |
| 5,797,951 A * | 8/1998 | Mueller | A61F 2/93 606/191 |
| 5,800,526 A | 9/1998 | Anderson et al. | |
| 5,824,037 A * | 10/1998 | Fogarty | A61F 2/07 623/1.13 |
| 5,843,164 A | 12/1998 | Frantzen et al. | |
| 5,984,955 A * | 11/1999 | Wisselink | A61F 2/07 623/1.35 |
| 6,066,168 A | 5/2000 | Lau et al. | |
| 6,071,308 A | 6/2000 | Ballou et al. | |
| 6,083,258 A | 7/2000 | Yadav | |
| 6,156,064 A | 12/2000 | Chouinard | |
| 6,165,214 A * | 12/2000 | Lazarus | A61F 2/07 128/898 |
| 6,264,684 B1 | 7/2001 | Banas et al. | |
| 6,273,909 B1 * | 8/2001 | Kugler | A61F 2/07 623/1.13 |
| 6,312,460 B2 | 11/2001 | Drasler et al. | |
| 6,331,188 B1 | 12/2001 | Lau et al. | |
| 6,334,867 B1 | 1/2002 | Anson | |
| 6,524,335 B1 | 2/2003 | Hartley et al. | |
| 6,565,596 B1 * | 5/2003 | White | A61F 2/07 623/1.13 |
| 6,652,580 B1 * | 11/2003 | Chuter | A61F 2/07 606/194 |
| 7,101,393 B2 | 9/2006 | Sarac | |
| 7,615,072 B2 | 11/2009 | Rust et al. | |
| 7,722,622 B2 | 5/2010 | Evans et al. | |
| 2001/0053930 A1 | 12/2001 | Kugler et al. | |
| 2002/0156523 A1 | 10/2002 | Lau et al. | |
| 2002/0177890 A1 | 11/2002 | Lenker | |
| 2003/0120338 A1 * | 6/2003 | Chobotov | A61F 2/07 623/1.36 |
| 2003/0199967 A1 | 10/2003 | Hartley et al. | |
| 2004/0082989 A1 * | 4/2004 | Cook | A61F 2/07 623/1.13 |
| 2006/0178733 A1 * | 8/2006 | Pinchuk | A61F 2/07 623/1.35 |
| 2007/0055347 A1 | 3/2007 | Arbefeuille | |

OTHER PUBLICATIONS

DACRON definition, Free Online Medical Dictionary, printed from web on Jan. 5, 2009.
International Search Report for International Application No. PCT/US03/22726, dated Dec. 2, 2003.
Office Action received in U.S. Appl. No. 10/624,864, dated Oct. 5, 2004.
Amendment and Interview Summary submitted in U.S. Appl. No. 10/624,864, dated Dec. 22, 2004.
Restriction Requirement received in U.S. Appl. No. 10/624,864, dated Mar. 24, 2005.
Amendment and Response to Restriction Requirement submitted is U.S. Appl. No. 10/624,864, dated Apr. 21, 2005.
Interview Summary received in U.S. Appl. No. 10/624,864, dated May 5, 2005.
Office Action received in U.S. Appl. No. 10/624,864, dated Sep. 9, 2005.
Amendments, Response to Office Action and Interview Summary submitted in U.S. Appl. No. 10/624,864, dated Sep. 22, 2005.
Office Action received in U.S. Appl. No. 10/624,864, dated Nov. 17, 2005.
Amendment and Response to Final Office Action submitted in U.S. Appl. No. 10/624,864, dated Jan. 9, 2006.

* cited by examiner

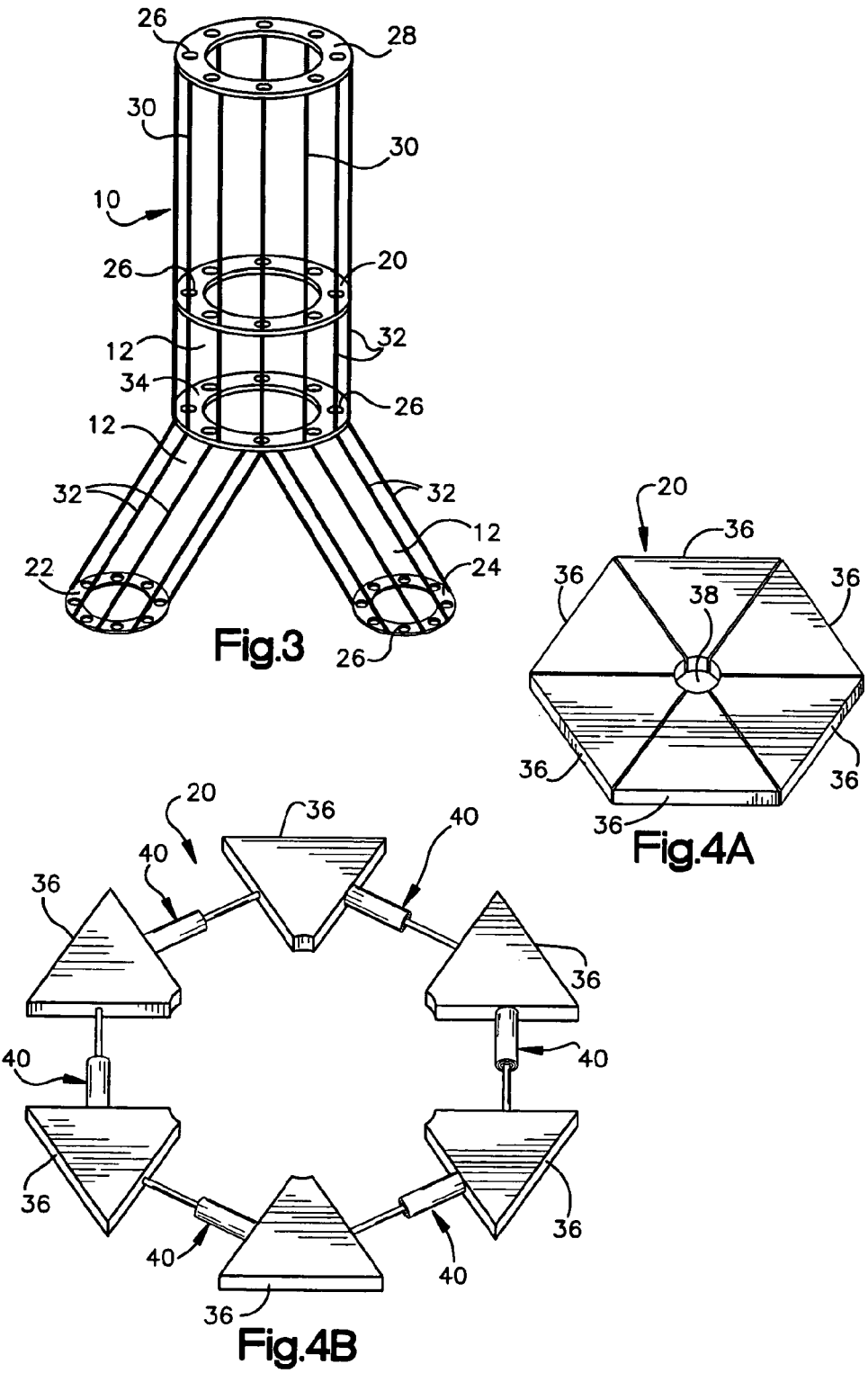

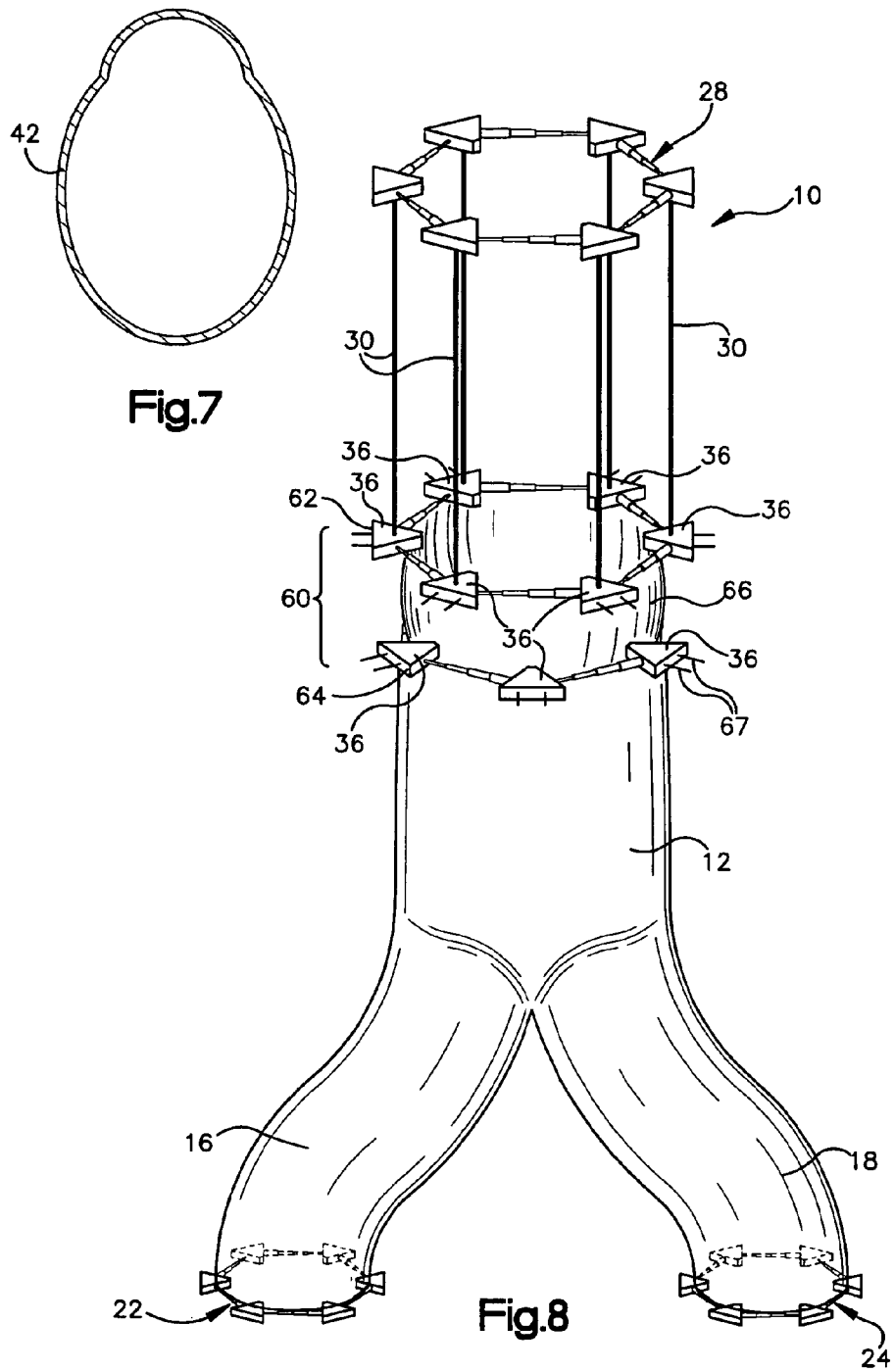

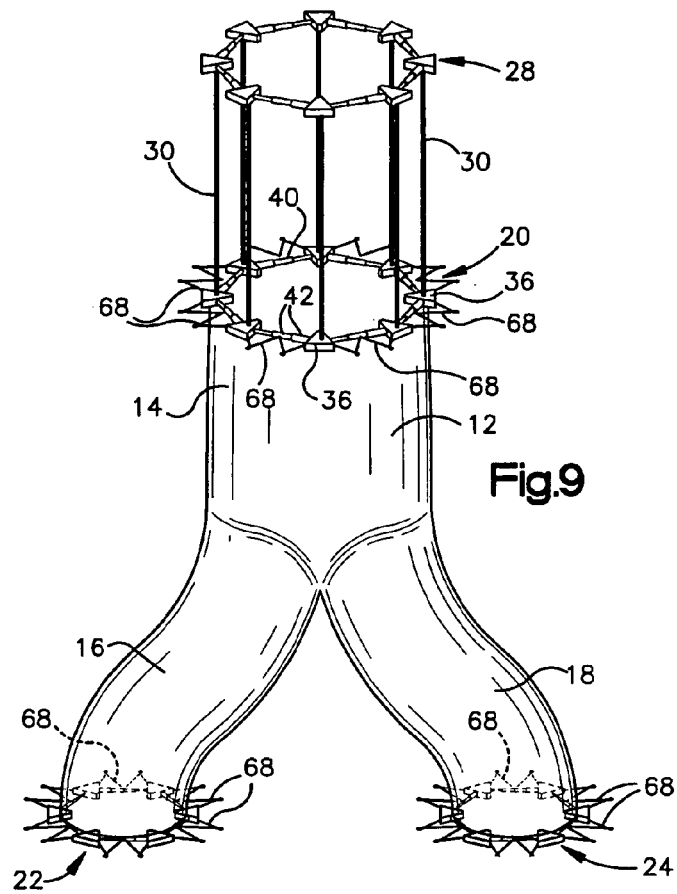
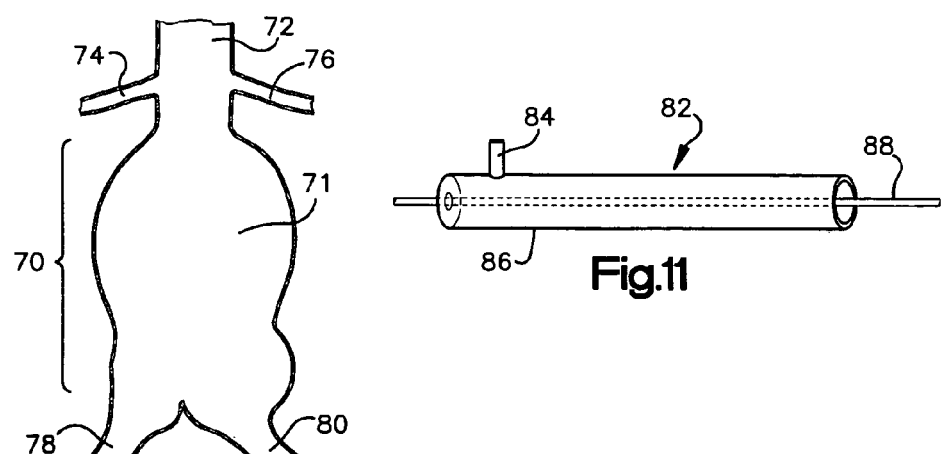

PERCUTANEOUS ENDOVASCULAR APPARATUS FOR REPAIR OF ANEURYSMS AND ARTERIAL BLOCKAGES

RELATED APPLICATIONS

This application is a continuation of, and claims priority to, U.S. patent application Ser. No. 11/484,331, filed 10 Jul. 2006; which claims priority to, and is a continuation-in-part of, U.S. patent application Ser. No. 10/624,864, filed 22 Jul. 2003, now U.S. Pat. No. 7,101,393; which in turn claims priority to U.S. Provisional Patent Application No. 60/397,745, filed 22 Jul. 2002. Each of the priority applications is hereby incorporated by reference in its entirety.

FIELD OF THE INVENTION

The present invention relates generally to an endovascular apparatus for the treatment of aneurysms or arterial blockages, and more particularly, to an endovascular apparatus having an expandable attachment device for securing the endovascular apparatus to an interior wall of a lumen.

BACKGROUND OF THE INVENTION

An abdominal aortic aneurysm is an abnormal enlargement or "ballooning out" of the arterial wall of the aorta in a region that passes through the abdominal cavity, usually below the renal arteries and above the common iliac arteries. The aneurysm may also extend into the common iliac arteries. Such aneurysms are typically brought on by the weakening of the arterial wall from vascular disease. Although abdominal aortic aneurysms often do not cause pain, unless treated, an aneurysm may rupture causing a fatal hemorrhage in a patient.

In the past aortic aneurysms were treated almost exclusively by surgical repair. Specifically, the aneurysm would be resected and replaced by an artificial artery known as a prosthetic graft. Because of the substantial risks associated with such an invasive surgery, however, other treatments for aortic aneurysms have been proposed including endovascular grafting.

Endovascular grafting involves the placement of a prosthetic graft within the lumen of the artery such that the graft spans the length of the aneurysm. In this manner the aneurysm can be excluded from the circulatory system rather than resected. Using a catheter as a deployment device, the endovascular graft can be introduced into the vascular system percutaneously. Once the graft has been positioned at the site of the aneurysm it can be attached to the vascular wall both above and below the aneurysm using expandable attachment devices to prevent movement of the graft after deployment.

To introduce an endovascular graft percutaneously, the graft must be collapsible into a small profile for negotiating the vascular system. Upon reaching the site of the aneurysm the graft and its attachment devices can be expanded into a desired shape using an inflating balloon catheter or other actuator. A variety of expandable attachment devices have been proposed for securing an endovascular graft to an interior wall of a vessel most of which use stents with hooks or barbs to penetrate the intima of the vessel. None of the proposed attachment devices, however, have been found to be ideally suited for use with an endovascular graft.

Accordingly an endovascular apparatus having a new expandable attachment device is desired. The new attachment device ideally should be small with a low profile and should expand to many times its initial diameter. It also should exert enough radial force when expanded to fix into the aorta and thereby reduce blood leaks around the apparatus.

SUMMARY OF THE INVENTION

In a first aspect, an expandable attachment device for securing an endovascular apparatus to an interior wall of a lumen is provided. The expandable attachment device may include a plurality of telescoping arms that are joined together to form an expandable ring. This ring may function similarly to stents. The expandable attachment device may be attached to an endovascular apparatus for the treatment of aneurysms or blockages, such as a graft or stent, or to a heart valve and may include barbs, hooks, or other fasteners about its perimeter for attaching to the interior wall of a lumen. Because the attachment device can be collapsed to a size that can be fed through a vessel, the attachment device and an associated endovascular apparatus can be deployed percutaneously in a patient. Once positioned at the site of an aneurysm or arterial blockage, the telescoping attachment device can be expanded to hold the endovascular apparatus in place adjacent the inner lumen wall.

In a second aspect, an endovascular apparatus is provided for treating aneurysms or arterial blockages using a minimally invasive technique. The apparatus includes a tubular sleeve having a cranial end and at least one caudal branch. If the tubular sleeve includes a first caudal branch and a second caudal branch then the tubular sleeve is shaped like an upside down "Y." Accordingly, for the treatment of abdominal aortic aneurysms the cranial end may be positioned in the infrarenal aorta, the first caudal branch may be positioned in one of the common iliac arteries, and the second caudal branch may be positioned in the other common iliac artery. The tubular sleeve may be made from materials conventionally used to make endovascular grafts including synthetic fabrics or films, DACRON™, (polyethylene terephthalate) or expanded polytetrafluoroethylene (ePTFE) so as to define a lumen and so as to be collapsible during percutaneous insertion into a patient's vascular system.

The endovascular apparatus further includes an expandable attachment device attached to the cranial end of the tubular sleeve for securing the apparatus to an interior wall of a vessel above an aneurysm. The expandable attachment device comprises a plurality of telescoping arms that are attached to form an expandable ring. Each telescoping arm is similar to an expandable presentation pointer. Alternatively, each telescoping arm may function like an accordion. Accordingly, during percutaneous insertion of the endovascular apparatus into a patient, the attachment device can be collapsed into a small profile. Once the apparatus is positioned at the site of the aneurysm or blockage, the expandable attachment device can be expanded to hold the endovascular apparatus in place adjacent the inner lumen wall. Fixation components may be positioned around the perimeter of the attachment device and may be partially embedded in the inner wall of the vessel to secure the attachment device.

The plurality of telescoping arms may be made from materials suitable for use in the human body including stainless steel, plastic, or an alloy of nickel and titanium generally known as NITINOL™. NITINOL is commonly used in the manufacture of medical devices that are to be deployed in a compressed state through a catheter because of its unique thermal memory properties. For example, a NITI- NOL part may be manufactured in a first condition and then cooled and compressed into a second condition. When heated to the body temperature of the patient the NITINOL part will expand to its original first condition.

In another aspect one or more expandable attachment devices may be attached to the one or more caudal branches of the tubular sleeve for securing the one or more caudal branches to the interior of the vessel wall.

BRIEF DESCRIPTION OF THE DRAWINGS

FIG. 3 is a schematic illustration of an endovascular apparatus according to a second aspect;

FIG. 4A is a top view of an expandable attachment device according to a first aspect in a fully collapsed state;

FIG. 4B is a top view of the expandable attachment device of FIG. 4A in a partially expanded state;

FIG. 7 is a cross section of a segment of a telescoping arm according to a first aspect;

FIG. 8 is an endovascular apparatus according to a third aspect;

FIG. 9 is an endovascular apparatus according to a fourth aspect;

FIG. 10 is an illustration of a typical abdominal aortic aneurysm located in the infrarenal aorta;

FIG. 11 is a catheter for percutaneous introduction of an endovascular apparatus into a body lumen;

DETAILED DESCRIPTION OF THE PREFERRED EMBODIMENT

Figure 1:
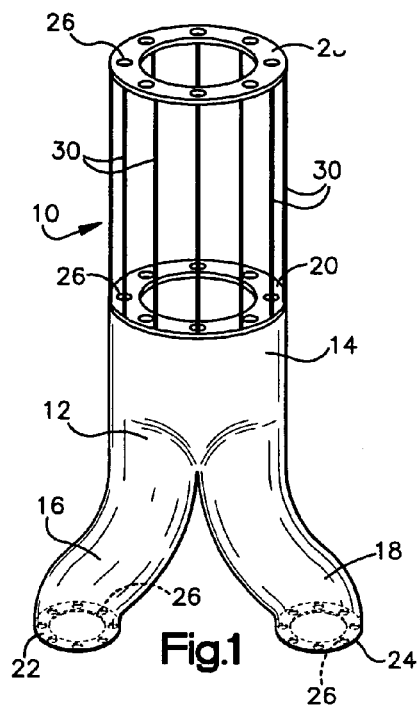
FIG. 1 is a schematic illustration of an endovascular apparatus according to a first aspect.

An endovascular apparatus 10 according to a first aspect is shown in FIG. 1. The endovascular apparatus 10 includes a tubular sleeve 12 having a cranial end 14, a first caudal branch 16, and a second caudal branch 18. In other embodiments, termed "uni-iliac" devices, the tubular sleeve 12 may include only a single caudal branch. The tubular sleeve may be made from DACRON, ePTFE, peritoneum, fascia, or other common graft material so as to form a flow path for by-passing an aneurysm.

The endovascular apparatus 10 further includes a first expandable attachment device 20 attached to the cranial end 14 of the tubular sleeve 12, a second expandable attachment device 22 attached to the first caudal branch 16 of the tubular sleeve 12, and a third expandable attachment device 24 attached to the second caudal branch 18 of the tubular sleeve 12. The expandable attachment devices 20, 22, 24 may include holes 26 which may be sewn or sutured to the tubular sleeve 12. Alternatively, in lieu of holes 26, the expandable attachment devices can be woven into the sleeve.

In another embodiment, the endovascular apparatus 10 may include a fourth expandable attachment device 28 that is attached to the first expandable attachment device 20 by support columns 30. The fourth expandable attachment device 28 may be positioned above a patient's renal arteries, superior mesenteric artery or celiac artery. The support columns 30, which may be made from NITINOL or stainless steel, may provide columnar support and strength for the endovascular apparatus 10 while permitting blood flow to arteries located between the first expandable attachment device 20 and the fourth expandable attachment device 28.

Figure 14:
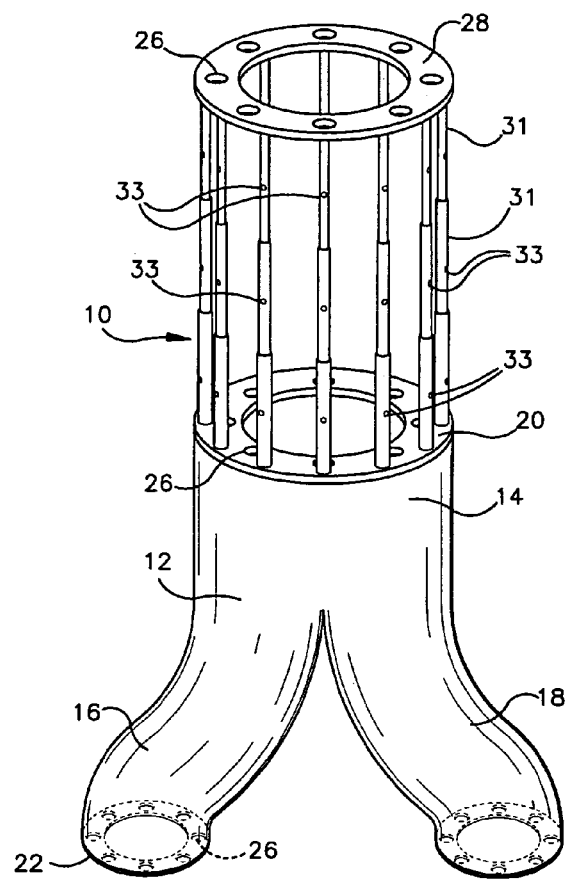
FIG. 14 is a schematic illustration of the endovascular apparatus of FIG. 1 having telescoping support columns.

The support columns 30 may be either wires or tubes. If tubular, the support columns 30 may also be telescoping. For example, in another embodiment depicted in FIG. 14, the support columns 31 may comprise a plurality of incrementally sized segments that are slideably engaged and fit within one another. Thus, in this embodiment the endovascular apparatus 10 may be inserted percutaneously into a vessel with the support columns 31 contracted such that the axial distance between the first expandable attachment device 20 and the fourth expandable attachment device 28 is reduced. During deployment of the endovascular apparatus 10 the support columns 31 may be expanded, thereby permitting the first expandable attachment device 20 to be positioned below the renal arteries while the fourth expandable attachment device is positioned above the renal arteries. In yet another embodiment, shown in FIG. 14, the tubular support columns 30, 31, whether telescoping or not telescoping, may contain an adhesive and include ports or apertures 33 such that the adhesive can escape the support columns 30, 31 upon deployment to assist in securing the endovascular apparatus 10 to the wall of a vessel.

Figure 2A:
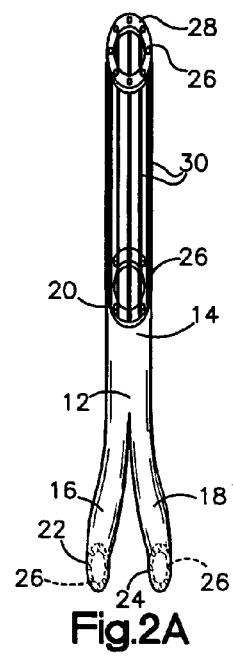
FIGS. 2A-D show the endovascular apparatus of FIG. 1 in various states or expansion.
Figure 2B:
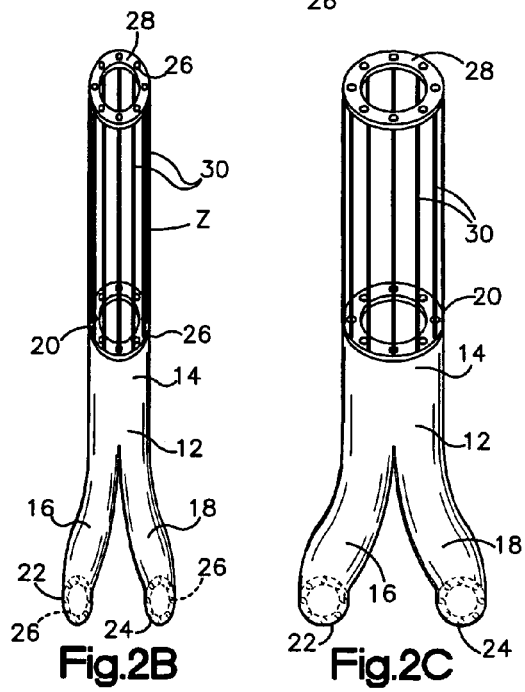
Figure 2C:
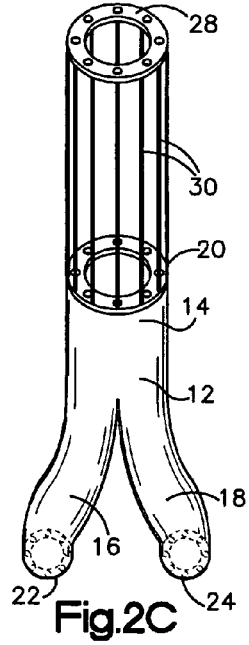
Figure 2D:
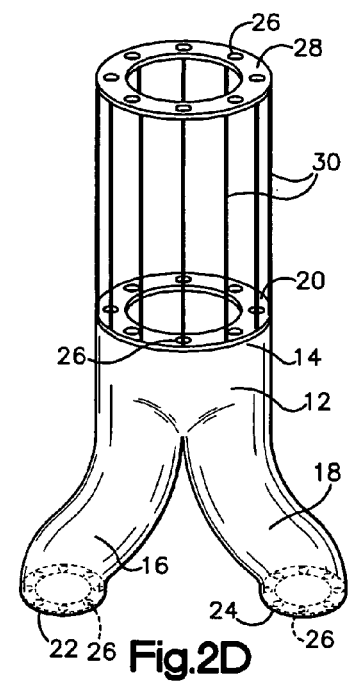

As illustrated in FIGS. 2A-2D, the endovascular apparatus 10 is collapsible for easy insertion and navigation through a patient's vascular system using a catheter. Particularly, as illustrated in FIG. 2A, the attachment devices 20, 22, 24, and 28 may be radially collapsed into a profile that is small enough to fit in a catheter sheath. When the attachment devices 20, 22, 24, 28 are deployed from the sheath at body temperature, the devices may be expanded by a balloon or other actuator to a size and shape in which they are able to retain the sleeve 12 against the wall of a vessel.

The endovascular apparatus 10 according to a second aspect is shown FIG. 3 in which the tubular sleeve 12 is supported by support columns 32. The support columns 32 may attach the first expandable attachment device 20 to a fifth expandable attachment device 34. Likewise, the support columns 32 may attach the second and third expandable attachment devices 22, 24 to the fifth expandable attachment device 34 which may be located at the juncture of the first caudal branch 16 and the second caudal branch 18 of the tubular sleeve 12. In addition the support columns 32 may be sewn or sutured to the exterior of the tubular sleeve 12. This may provide continued columnar support throughout the endovascular apparatus 10 to prevent migration within the vessel. The support columns 32 may be telescoping as described with respect to FIG. 14.

Figure 4C:
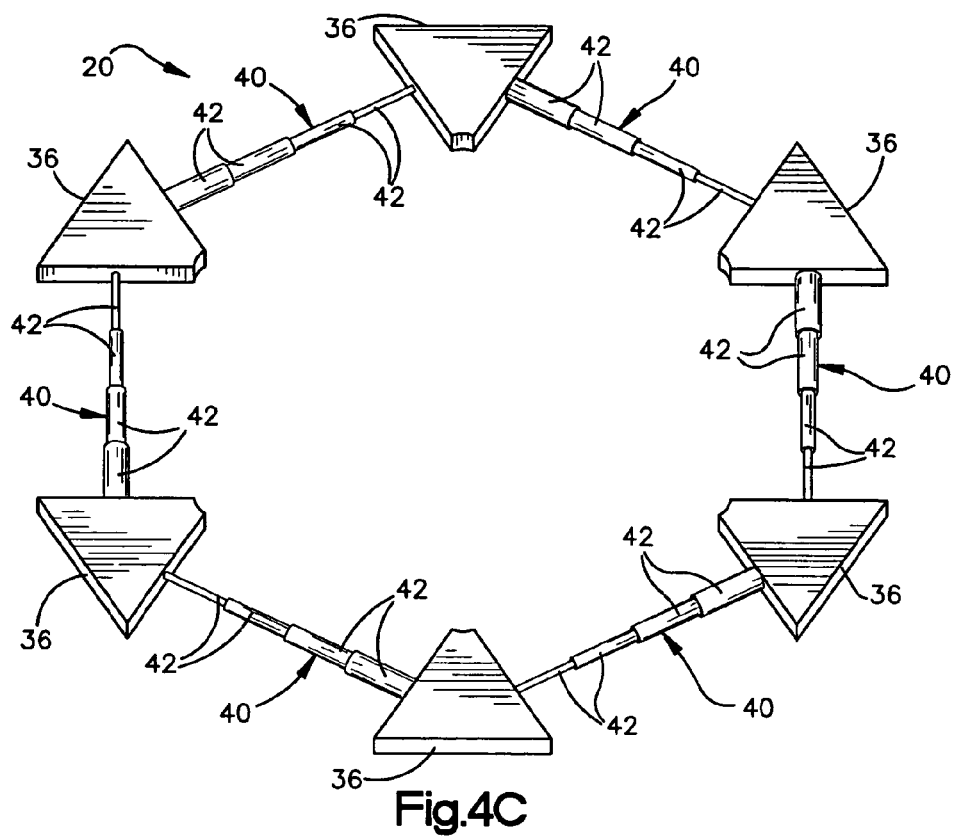
FIG. 4C is a top view of the expandable attachment device of FIG. 4A in a fully expanded stated.

Referring to FIG. 4A, an expandable attachment device 20 according to a first aspect is shown in a fully collapsed state. The attachment device 20 includes a plurality of fixation components 36 positioned about the perimeter of the device 20. A port 38 is located at the center of the attachment device 20. The port 38 is sized so as to receive a balloon or other actuator during deployment. The balloon may be inflated to expand the attachment device 20 after insertion into a vessel. FIG. 4B shows the attachment device 20 in a partially expanded state. FIG. 4C shows the attachment device 20 in a fully expanded state. While in a preferred embodiment, the fixation component can have angular corners, in other embodiments, the fixation component can have curved, rounded, or ovoid edges. Similarly, the entire corner or edge of each fixation component need not be the same shape throughout the length of the edge or corner.

Figure 16:
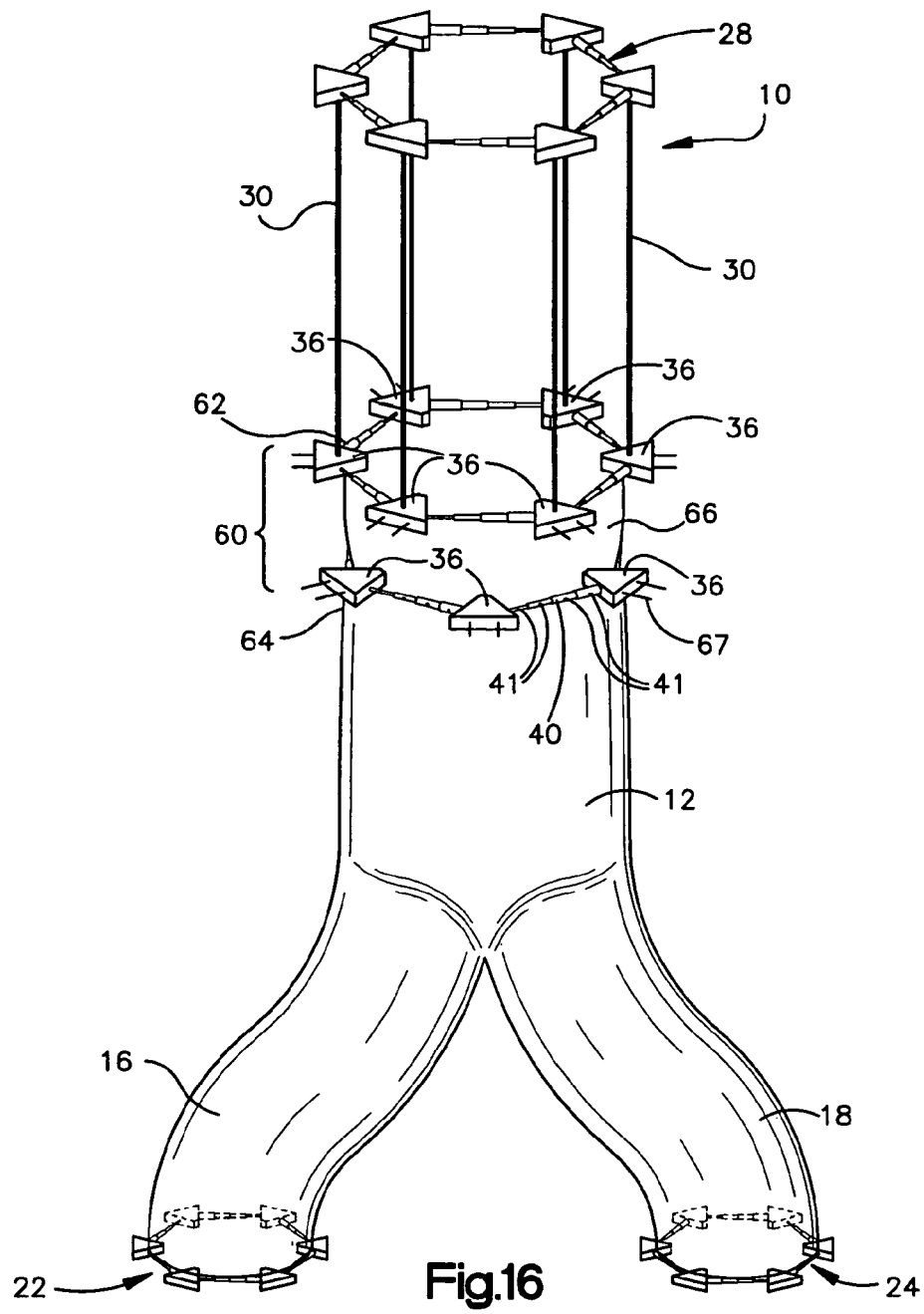
FIG. 16 is a schematic illustration of an expandable attachment device according to another aspect.

Referring to FIG. 4C, a telescoping arm 40 is used to attach each fixation component 36 to an adjacent fixation component 36. The telescoping arm 40 may be pivotably attached to a fixation component 36 at one or both ends of the arm 40. A telescoping arm 40 is made up of a plurality of segments 42. The segments 42 may be in slideable contact with one another and may be incrementally sized so as to fit within one another. For example, each telescoping arm 40 may be constructed from what is referred to generally as "nested tubes." When the telescoping arms 40 are fully extended the attachment device 20 may resemble a polygon having fixation components 36 located at its vertices. The fixation components 36 may include barbs or prongs 67 (shown in FIG. 8) for fixation to a vessel wall. In another embodiment shown in FIG. 16, the telescoping arms 40 may contain an adhesive and include ports or apertures 41 such that the adhesive can escape the telescoping arms upon deployment to assist in securing the endovascular apparatus 10 to the wall of a vessel.

Figure 13A:
FIGS. 13A-G are schematic top views of an expandable attachment device according to a third aspect in various states of expansion.
Figure 13H:
FIGS. 13H-N are schematic side views of the expandable attachment device of FIGS. 13A-G.
Figure 13O:
FIGS. 13O-T are schematic isometric views of the expandable attachment device of FIGS. 13A-G.
Figure 13B:
Figure 13I:
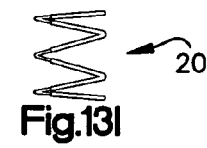
Figure 13P:
Figure 13C:
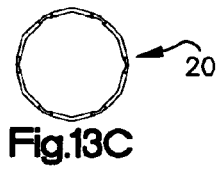
Figure 13J:
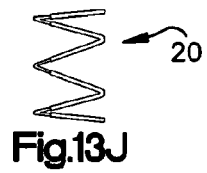
Figure 13Q:
Figure 13D:
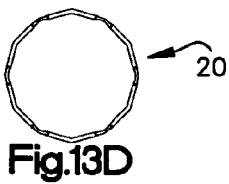
Figure 13K:
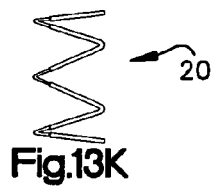
Figure 13R:
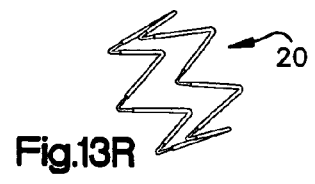
Figure 13E:
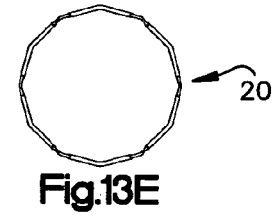
Figure 13L:
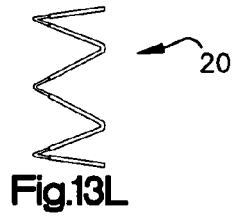
Figure 13S:
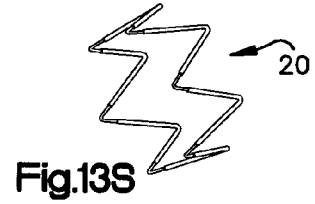
Figure 13F:
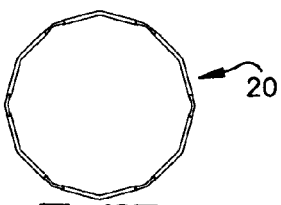
Figure 13M:
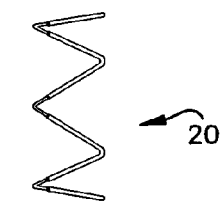
Figure 13T:
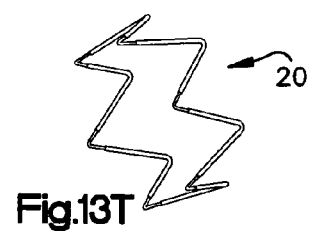
Figure 13G:
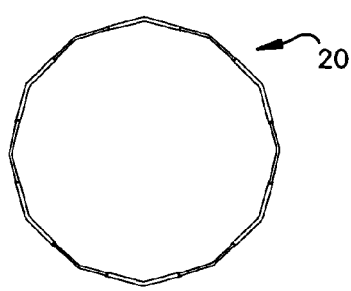
Figure 13N:
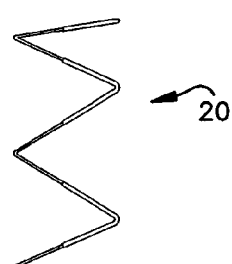

As one of ordinary skill might appreciate, the attachment device may take variety of shapes depending upon the configuration of the telescoping arms 40 and the fixation components 36. For example, referring to FIGS. 12A-D, the telescoping arms 40 may be positioned in a single plane. Alternatively, referring to FIGS. 13A-T, the telescoping arms 40 may be positioned in multiple planes in, for example, what is referred to herein as an "M configuration." One possible advantage of the M configuration is that it may produce superior radial force for holding the attachment device in position. In addition, the M configuration may produce the same ratio of expansion (i.e., the ratio of the final outer diameter of the attachment device in its expanded state to the initial outer diameter of the attachment device in its collapsed state) as the "single plane configuration" using fewer parts.

Figure 13U:
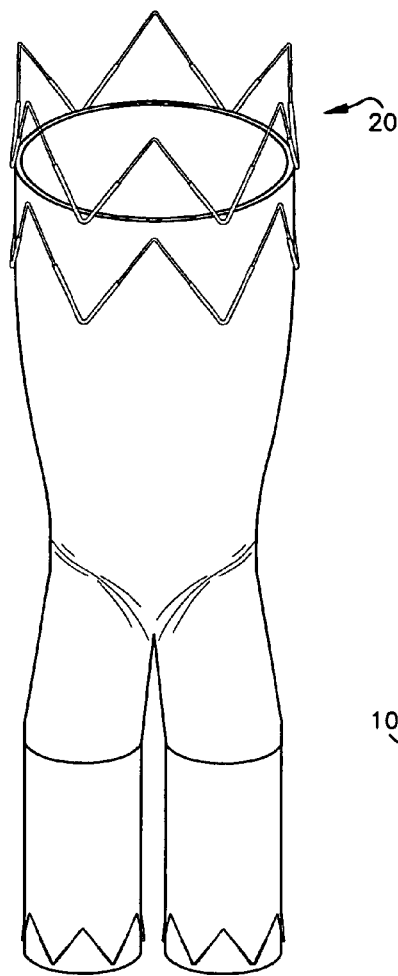
FIG. 13U is a schematic illustration of another embodiment of the invention.

FIG. 13U depicts multiple "M configuration" attachment devices on an endovascular apparatus.

Figure 5:
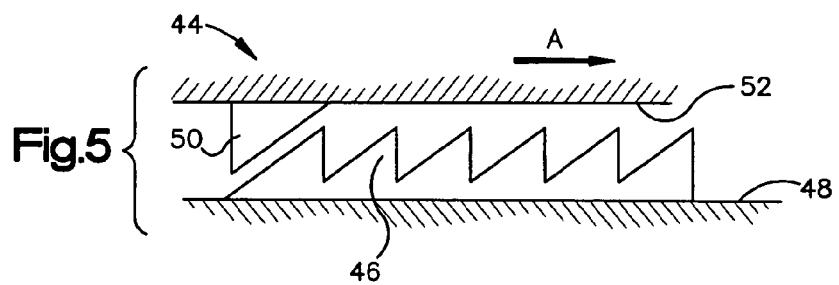
FIG. 5 is a locking mechanism according to a first aspect in a first position.
Figure 6:
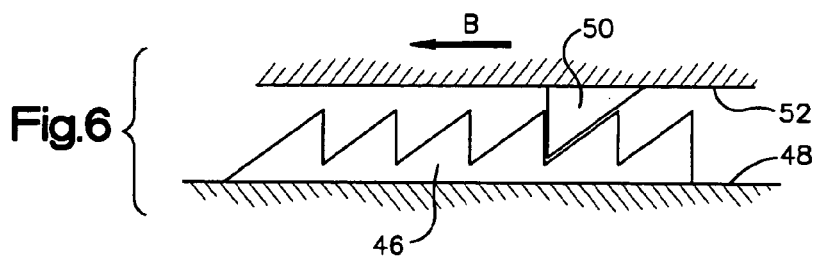
FIG. 6 is the locking mechanism of FIG. 5 in a second position.
Figure 12A:
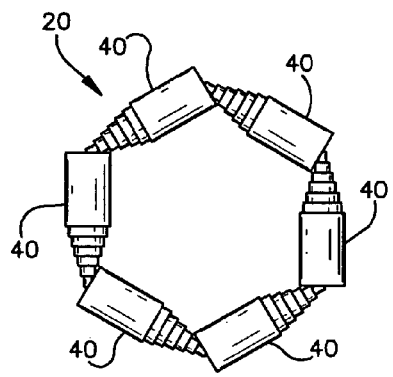
FIG. 12A is a schematic top view of an expandable attachment device according to a second aspect in a partially expanded state.
Figure 12C:
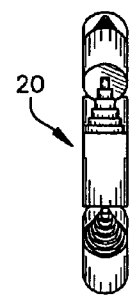
FIG. 12C is a schematic side view of the expandable attachment device of FIG. 12A.
Figure 12B:
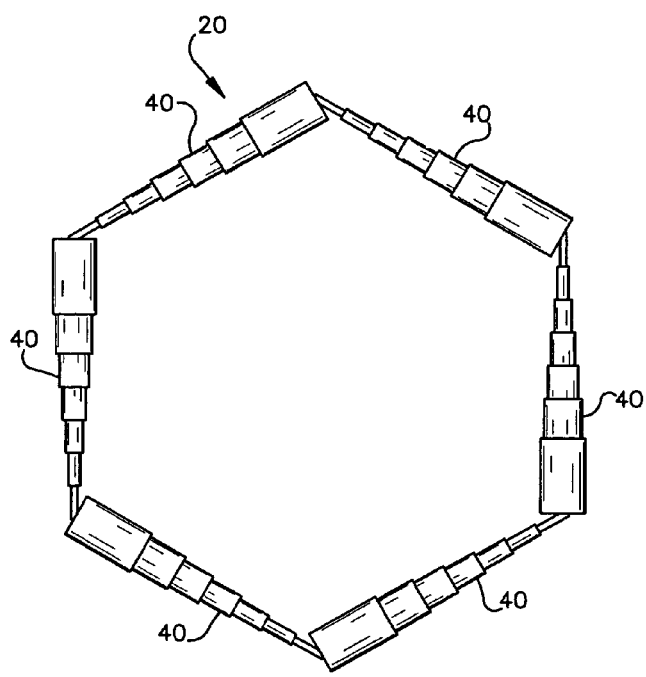
FIG. 12B is a schematic top view of the expandable attachment device of FIG. 12A in a fully expanded stated.
Figure 12D:
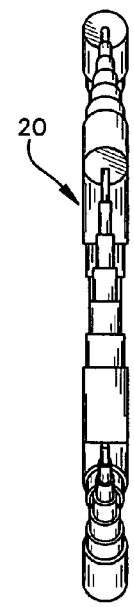
FIG. 12D is a schematic side view of the expandable attachment device of FIG. 12B.

To keep the telescoping arms 40 in their final extended state after deployment in a vessel, a one-way latch may be used to lock adjacent segments 42. FIG. 5 shows one possible latch 44, in a first position, for locking the telescoping arms 40. The latch 44 may consist of a one or more grooves 46 associated with a first segment 48 and a tooth 50 associated with a second, adjacent segment 52. As the telescoping arm 40 is expanded, the second segment 52 moves in a first direction A relative to the first segment 48. The tooth 50 and the grooves 46 are aligned so as to engage when the telescoping arm 40 is extended. Once the tooth 50 engages a groove 46, as shown in FIG. 6, the second segment 52 may not move in a second direction B relative to the first segment 48. Accordingly, the telescoping arm 40 is free to extend but may not collapse once extended. Of course other one-way latches may be used to lock the segments 42 of the telescoping arms 40. FIG. 7 illustrates one possible cross-section of a segment 42 of the telescoping arm 40. This "rail" design permits room for sliding and positioning of a one-way latch, like the one shown in FIG. 5, between segments 42 shown in FIG. 4.

FIG. 8 shows the endovascular apparatus 10 according to a third aspect. In the embodiment shown in FIG. 8, the endovascular apparatus 10 includes a double-expandable attachment device 60 in the place of the first expandable attachment device 20. The double-expandable attachment device 60 comprises an upper expandable attachment device 62 and a lower expandable attachment device 64 which are separated by and attached to an o-ring seal 66. The upper attachment device 62 is angularly offset from the lower attachment device 64 so that the fixation components 36 of each are offset. The fixation components 36 may include prongs or barbs 67 to aid in securing the expandable attachment devices 62, 64 to the vessel wall. This design provides for secure attachment to the vessel wall with reduced leakage around the perimeter of the attachment device 60. The lower expandable attachment device 64 may be attached to the tubular sleeve 12. The upper expandable attachment device 62 may be attached to the fourth expandable attachment device 28 by support columns 30.

Figure 15:
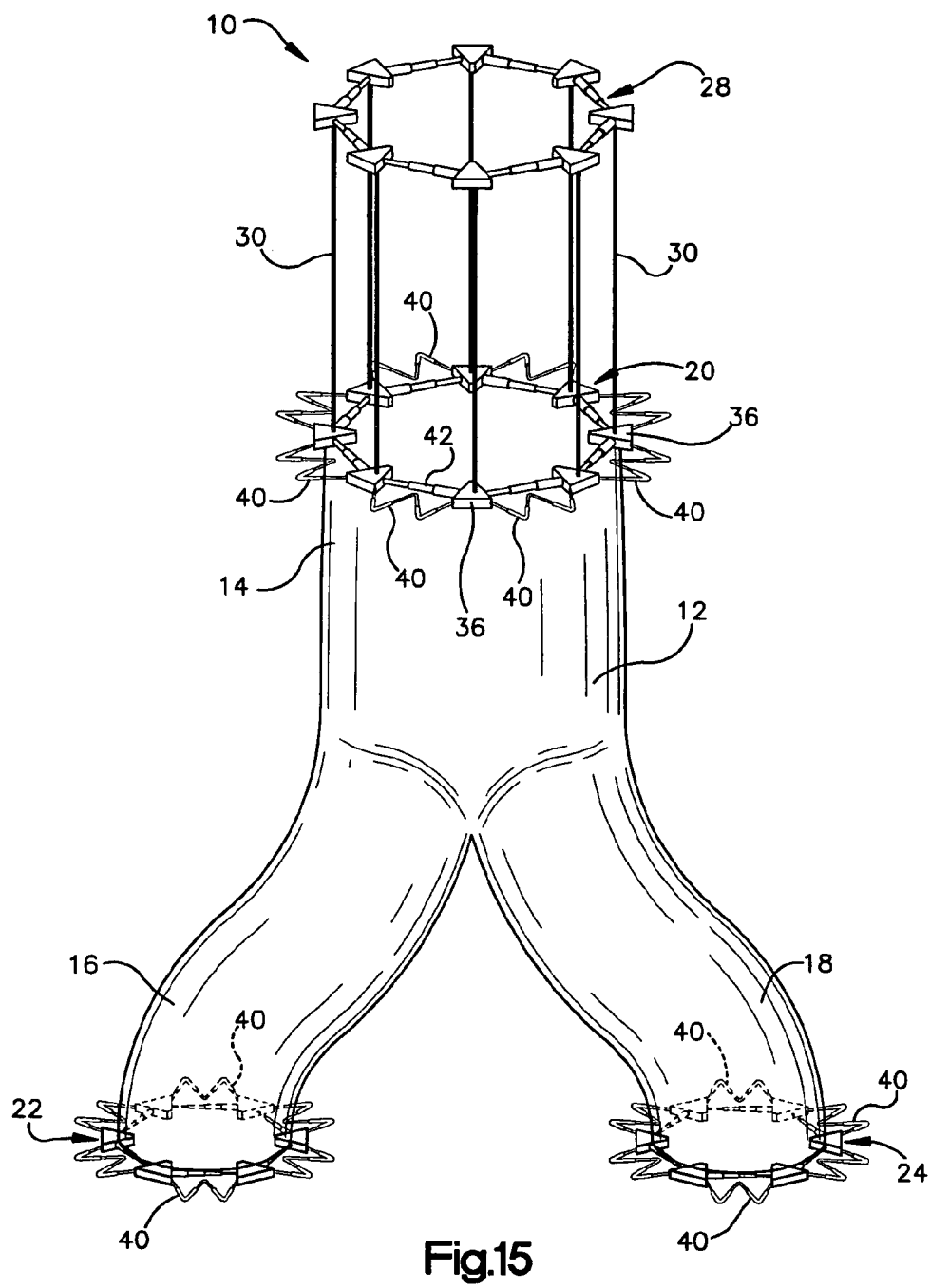
FIG. 15 is a schematic illustration of an endovascular apparatus according to another aspect.

Referring to FIG. 9, the endovascular apparatus 10 according to fourth aspect is shown. In this embodiment a plurality of "M springs" 68 are attached to the cranial end 14 of tubular sleeve 12 as graft expanders in order to hold the tubular sleeve 12 open. In this manner the M springs 68 may reduce leakage around the perimeter of the tubular sleeve 12. M springs 68 may also be used to hold the caudal ends 16, 18 of the tubular sleeve 12 open. In the embodiment shown in FIG. 9, the M springs 68 are not attached to the segments 52 of the telescoping arms 40 and are located on the exterior of the tubular sleeve 12. In another embodiment, the M springs 68 may be located on the interior of the tubular sleeve 12 or attached to the fixation components 36. Of course, in place of the "M springs" 68, springs in the shape of a "V" may be used. Alternatively, in another embodiment depicted in FIG. 15, the M springs 68 may be replaced by telescoping arms 40 in an "M configuration."

FIG. 10 illustrates a typical abdominal aortic aneurysm 70 located in the infrarenal aorta 71. The infrarenal aorta 71 is that portion of the aorta 72 located below the renal arteries 74, 76. As shown in FIG. 10, abdominal aortic aneurysms typically occur below the renal arteries 74, 76 and above the common iliac arteries 78, 80. In some cases, the aneurysm includes the common iliac arteries 78, 80. The endovascular apparatus 10 may be used to treat or repair an abdominal aortic aneurysm 70, like the one shown in FIG. 10, by excluding the weakened aneurysmal aortic wall from pressurized and pulsatile flow. In addition, the endovascular apparatus 10 may be used to treat aneurysms or blockages located in other body lumens such as the thoracic aorta, iliac arteries, subclavian arteries, urinary tract, bile tract, intestinal tract, etc.

Figure 17:
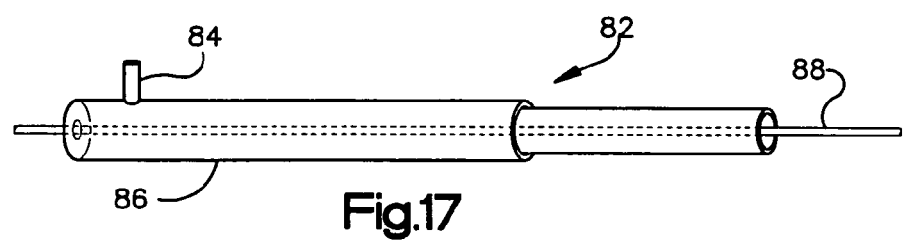
FIG. 17 is a schematic illustration of a telescoping catheter for percutaneous introduction of an endovascular apparatus into a body lumen.

The endovascular apparatus 10 may be deployed at the site of an aneurysm percutaneously using a catheter 82 like the one shown in FIG. 11. The catheter 82 may have an IV port 84, a sheath 86 and an introducer 88 which can be withdrawn within the sheath 86. Using the catheter 82, the device can be introduced percutaneously through either of the femoral arteries. As shown in FIG. 17, using a "nested tube" design similar to the one utilized by the telescoping arms 40 of the attachment device 20, the catheter 82 may also be made to be telescoping.

During deployment the first expandable attachment device 20 may be positioned just below the renal arteries 74, 76 and seated with an expandable balloon or other actuator. The fourth expandable attachment device 28 may be positioned superior to the renal arteries 74, 76, the mesenteric artery, or the celiac artery and seated with an expandable balloon. After the first attachment device 20 is seated, the second expandable attachment device 22 may be positioned in a first iliac artery 78 and seated with an expandable balloon or other actuator. The third expandable attachment device 24 may be positioned such that it rests at a second iliac artery 80. To position and seat the third attachment device 24, access may be obtained percutaneously through the second iliac artery 80.

What is claimed is:

1. An endovascular apparatus comprising:
    a tubular sleeve having a central lumen extending longitudinally between a cranial end portion and a caudal end portion, the cranial end portion including a cranial end opening and the caudal end portion including at least one caudal end opening; and
    a double-expandable attachment device extending circumferentially around the cranial end opening of the tubular sleeve, the double-expandable attachment device including:
    an upper expandable attachment device including a plurality of fixation components configured to fix the apparatus to a vessel wall and positioned about the perimeter of the upper expandable attachment device, and a plurality of circumferentially extending arms, each arm being used to attach each fixation component to a circumferentially adjacent fixation component,
    a lower expandable attachment device including a plurality of fixation components configured to fix the apparatus to a vessel wall and positioned about the perimeter of the lower expandable attachment device, and a plurality of circumferentially extending arms, each arm being used to attach each fixation component to a circumferentially adjacent fixation component, the lower expandable attachment device connecting the double-expandable attachment device to the cranial end opening of the tubular sleeve, and
    an o-ring seal located longitudinally between, and connecting the upper expandable attachment device and the lower expandable attachment device, the o-ring seal being configured to reduce leakage around the perimeter of the double-expandable attachment device at the cranial end opening.

2. The endovascular apparatus of claim 1, wherein the caudal end portion of the tubular sleeve includes a first caudal branch laterally separated from a second caudal branch, the first and second caudal branches each including a branch opening oriented in a caudal direction.

3. The endovascular apparatus of claim 2, wherein at least one of the first and second caudal branches includes a branch expandable attachment device extending circumferentially therearound and attached thereto.

4. The endovascular apparatus of claim 3, wherein each branch expandable attachment device includes:
    a plurality of fixation components positioned about the perimeter of the expandable attachment device; and
    a plurality of circumferentially extending arms, each arm being used to attach each fixation component to a circumferentially adjacent fixation component.

5. The endovascular apparatus of claim 1, wherein the caudal end opening includes a caudal end expandable attachment device extending circumferentially around the caudal end portion of the tubular sleeve.

6. The endovascular apparatus of claim 5, wherein the caudal end expandable attachment device includes:
    a plurality of fixation components positioned about the perimeter of the expandable attachment device; and
    a plurality of circumferentially extending arms, each arm being used to attach each fixation component to a circumferentially adjacent fixation component.

7. The endovascular apparatus of claim 1, wherein at least the arms of the double-expandable attachment device are selectively collapsible in the circumferential direction to selectively and reversibly reduce a total circumference of the double-expandable attachment device from an expanded apparatus condition to a collapsed apparatus condition.

8. The endovascular apparatus of claim 4, wherein at least the arms of the branch expandable attachment device are selectively collapsible in the circumferential direction to selectively and reversibly reduce a total circumference of the branch expandable attachment device from an expanded apparatus condition to a collapsed apparatus condition.

9. The endovascular apparatus of claim 6, wherein at least the arms of the caudal end expandable attachment device are selectively collapsible in the circumferential direction to selectively and reversibly reduce a total circumference of the caudal end expandable attachment device from an expanded apparatus condition to a collapsed apparatus condition.

10. The endovascular apparatus of claim 1, wherein at least one circumferentially extending arm of the double-expandable attachment device is a telescoping arm having a plurality of segments in slideable contact with one another.

11. The endovascular apparatus of claim 4, wherein at least one circumferentially extending arm of the branch expandable attachment device is a telescoping arm having a plurality of segments in slideable contact with one another.

12. The endovascular apparatus of claim 6, wherein at least one circumferentially extending arm of the caudal end expandable attachment device is a telescoping arm having a plurality of segments in slideable contact with one another.

* * * * *